United States Patent
Iida et al.

(10) Patent No.: US 6,599,360 B2
(45) Date of Patent: Jul. 29, 2003

(54) SILICON WAFER, METHOD FOR DETERMINING PRODUCTION CONDITIONS OF SILICON SINGLE CRYSTAL AND METHOD FOR PRODUCING SILICON WAFER

(75) Inventors: Makoto Iida, Gunma (JP); Masanori Kimura, Gunma (JP)

(73) Assignee: Shin-Etsu Handotai Co., Ltd., Tokyo (JP)

( * ) Notice: Subject to any disclaimer, the term of this patent is extended or adjusted under 35 U.S.C. 154(b) by 0 days.

(21) Appl. No.: 09/936,920

(22) PCT Filed: Jan. 18, 2001

(86) PCT No.: PCT/JP01/00302

§ 371 (c)(1),
(2), (4) Date: Sep. 20, 2001

(87) PCT Pub. No.: WO01/55485

PCT Pub. Date: Aug. 2, 2001

(65) Prior Publication Data

US 2003/0015131 A1 Jan. 23, 2003

(51) Int. Cl.[7] ............................................... C30B 15/02

(52) U.S. Cl. ..................................................... 117/19

(58) Field of Search ............................ 117/13, 14, 20

(56) References Cited

FOREIGN PATENT DOCUMENTS

| JP | A 4-192345 | 7/1992 |
| JP | A 11-274163 | 10/1999 |
| JP | A 2000-7486 | 1/2000 |
| WO | WO 01/16410 A1 | 3/2001 |

OTHER PUBLICATIONS

Japanese Journal of Applied Physics, Part 1 Regular Papers, Short Notes & Review Papers, Sep. 1993, vol. 32, No. 9A.
Dupret et al., "Global modeling of heat transfer in crystal growth furnaces" Int. J. Heat Mass Transfer., vol. 33, No. 9, pp. 1849–1871, 1990.
Ohashi et al., "Nitrogen Doping Grows–in Defects Engineering in Czochralski Silicon Crystals", Academia Forum 99, Nov. 24–26, 1999.
Nakaumura et al., "The Effect of Nitrogen on the Grown–in Defect Formation in CZ Silicon Crystals", Komatsu Electronic Metals Co., Ltd.

*Primary Examiner*—Felisa Hiteshew
(74) *Attorney, Agent, or Firm*—Oliff & Berridge, PLC

(57) ABSTRACT

According to the present invention, there are provided a silicon wafer, wherein an epi-layer is not formed on a surface, and number of LSTDs having a size of 50 nm or more existing in a surface layer portion is 0.24 number/$cm^2$ or less; a method for determining production conditions of a silicon single crystal, which comprises pulling nitrogen-doped silicon single crystals by the CZ method while varying V/G and/or PT, producing silicon wafers from the silicon single crystals, subjecting the silicon wafers to a heat treatment, determining acceptability of the wafers based on a predetermined characteristic value, obtaining correlation between the acceptability and V/G and PT, and determining production conditions based on the correlation; and a method for producing a silicon wafer comprising pulling a silicon single crystal so that V/G and PT should be lower than V/G and shorter than PT that are uniquely defined by predetermined nitrogen concentration and oxygen concentration in the silicon single crystal, conditions of heat treatment to which the silicon wafer is subjected, and grown-in defect density of the silicon wafer. According to the present invention, a nitrogen-doped annealed wafer showing a low defect density even under severe examination conditions and little fluctuation thereof depending on the production condition is produced.

25 Claims, 7 Drawing Sheets

SILICON WAFER, METHOD FOR DETERMINING PRODUCTION CONDITIONS OF SILICON SINGLE CRYSTAL AND METHOD FOR PRODUCING SILICON WAFER

This Application is a PCT/JP01/00320 Jan. 18, 2001.

TECHNICAL FIELD

The present invention relates to a silicon wafer having a grown-in defect density lower than that of conventional epitaxial wafers, annealed wafers and wafers having an N-region for entire plane, a method for determining production conditions of the same and a method for producing the same. The present invention further relates to a method for determining production conditions of a silicon single crystal that is for stable production of silicon wafers of low grown-in defect density, which-wafers are produced by subjecting silicon wafers produced from a nitrogen-doped silicon single crystal to heat treatment, and a method for producing the same.

BACKGROUND ART

In recent years, in connection with use of finer circuit elements accompanying the use of higher integration degree of semiconductor circuits, the demand for quality of silicon single crystals produced by the CZ method, from which substrates of the circuit are produced, has become higher. In particular, there are defects generated during the crystal growth, which are called grown-in defects including FPD (Flow Pattern Defect), LSTD (Laser Scattering Tomography Defect), COP (Crystal Originated Particle) and so forth, and degrade oxide dielectric breakdown voltage characteristics, device characteristics and so forth, and reduction of them has been considered important.

Therefore, there have been developed several kinds of wafers produced form of crystals having few grown-in -defects, including epitaxial wafer consisting a usual silicon wafer on which a silicon layer is newly provided by epitaxial growth, annealed wafers which is produced by subjecting wafers to heat treatments at a high temperature in hydrogen or argon atmospheres, wafers having an N-region (a region free from dislocation clusters existing outside the QSF ring) for entire plane which are produced by improving the growth conditions of CZ—Si single crystals and so forth.

In addition, it is required to impart gettering ability to such wafers in order to eliminate contamination by impurities introduced during the device production process. To answer to this requirement, there have been also developed wafers imparted with the IG (Intrinsic Gettering) effect by using additional heat treatment, or doping impurities such as nitrogen or carbon to accelerate oxygen precipitation in bulk portions.

Among these, the wafers obtained by annealing nitrogen-doped wafers (referred to as "nitrogen-doped annealed wafers" hereinafter) are extremely useful as wafers showing reduced grown-in defects in wafer surface layer portions and high density of BMD (Bulk Micro Defect) in bulk portions. These are wafers developed by utilizing the defect agglomeration inhibition effect and the oxygen precipitation promotion effect of nitrogen doping, and since they have a smaller defect size compared with usual crystals, they show good efficiency for eliminating the defects in surface layers by annealing and they are wafers of effective gettering ability also showing a high BMD density in bulk portions.

However, if a highly precise defect evaluation apparatus such as MO-601 (produced by Mitsui Mining and Smelting Co., Ltd.) is used, it can be seen that these silicon wafers referred to with the term low defect also have defects, although their density is low. The apparatus MO-601 is a highly precise defect evaluation apparatus, which can measure even extremely fine defects having a size of about 50 nm, and also has a function enabling evaluation of defects along the depth direction for a depth of 5 $\mu$m.

According to evaluation of defects having a size 50 nm or more (LSTD) for a depth of, for example, 5 $\mu$m by using such a defect evaluation apparatus, it can be seen that there are defects in a density of about 40 number/6" wafer (0.23 number/cm$^2$) in usual epitaxial wafers and nitrogen-doped wafers undergone epitaxial growth, about 3000 number/6" wafer (17 number/cm$^2$) in annealed wafers, and about 70/6" wafer (0.40 number/cm$^2$) in wafers having an N-region for entire plane and nitrogen-doped wafers having an N-region for entire plane. Since these defects have an extremely small size, they do not cause any problem in many cases in the present device production process of the usual level. However, they are considered to inevitably cause a problem for the currently latest devices or devices expected to be produced in future.

Among these low defect wafers, the nitrogen-doped annealed wafers have the aforementioned useful effects, i.e., the grown-in defect agglomeration inhibition effect and the oxygen precipitation promotion effect, and in addition, they undergo the annealing process that eliminates defects, which is not used for epi-wafers or improved CZ wafers. Therefore, they are considered to have high potential as for reduction of grown-in defects in a considerable degree. However, the current nitrogen-doped annealed wafers shows significant fluctuation in the defect density for every production lot, and it was found that they contained defects at a level of at least about 140 number/6" wafer (0.79 number/cm$^2$) according to a measurement using the aforementioned MO-601. In order to further reduce these defects to stably produce wafers of low defect density, it is necessary to develop crystal growth conditions and annealing conditions in good balance.

Meanwhile, the nitrogen-doped CZ crystals, which are used as the raw material of nitrogen-doped annealed wafers, recently come to be actively studied, and researches about the grown-in defect agglomeration inhibition effect and the oxygen precipitation promotion effect have progressed. However, data have been scarcely obtained concerning if thermal history during the pulling of crystals affects on the formation of grown-in defects in nitrogen-doped crystals in a manner similar to that of non-nitrogen-doped crystals, or if it affects in a manner different much or less. Therefore, it is expected that, even though the annealing conditions are fixed, significant fluctuation of the detect elimination effect after the annealing would be observed, if the pulling conditions of nitrogen-doped crystals such as the thermal history during pulling of the crystals are changed.

In order to ameliorate such fluctuation, it is expected to employ an approach of eliminating more defects by annealing to obtain an extremely low defect density. However, it is not desirable to adopt such an approach because it requires costly annealing (annealing at high temperature for long time). Therefore, the defects should be controlled by the crystal pulling conditions. However, the crystal growth conditions have not been fully studied as described above, and claptrap development has been conducted so far, in which, for example, a crystal was pulled with some growth conditions, wafers are produced and annealed, and then it was confirmed if a necessary grown-in defect (mainly void defect) free region could be secured in the wafers. Thus, development cost might become high, and quality was not stabilized.

Further, since the thermal history also varies depending on the diameter of crystal, the annealing conditions may also be changed depending on it, and the crystal must be optimized for each annealing condition. However, sufficient researches have not been conducted also in this respect.

DISCLOSURE OF THE INVENTION

Therefore, the present invention was accomplished in view of the aforementioned problems, and its object is to produce a nitrogen-doped annealed wafer showing a low defect density and little fluctuation depending on production conditions by controlling grown-in defects in a nitrogen-doped crystal, which serves as a raw material of the nitrogen-doped annealed wafer.

Another object of the present invention is to provide a silicon wafer having extremely few surface defects in spite of not forming an epitaxial layer that invites increase of cost.

The present invention for achieving the aforementioned objects provides a silicon wafer, wherein an epitaxial layer is not formed on a surface, and LSTDs having a size of 50 nm or more existing in a surface layer portion are fewer than those existing in a surface layer portion of an epitaxial layer of a silicon epitaxial wafer.

The silicon wafer of the present invention can be a silicon wafer in which LSTDs existing in a surface layer portion are fewer than those existing in a surface layer portion of an epitaxial layer of an epitaxial wafer in spite of not forming an epitaxial layer on the surface, and it provides an advantage that it does not require any heat treatment for epitaxial growth that takes a long period of time.

In this case, the aforementioned surface layer portion may be a region having a depth of at least 5 $\mu$m from the wafer surface.

Such a depth is defined because, if the surface layer portion containing extremely few defects consists of a region having a depth of at least 5 $\mu$m from the wafer surface, it would be sufficient for producing, devices on the wafer surface.

The present invention also provides a silicon wafer, wherein an epitaxial layer is not formed on a surface, and number of LSTDs having a size of 50 nm or more existing in a surface layer portion is 0.23 number/cm$^2$ or less.

The silicon wafer of the present invention can also be a silicon wafer containing few defects comparable to those of an epitaxial wafer or fewer defects than those of an epitaxial wafer in spite of not forming an epitaxial layer on the surface. Therefore, it does not require the epitaxial growth process, and thus productivity and cost of highly integrated devices are improved.

In this case, the aforementioned surface layer portion may be region having a depth of at least 5 $\mu$m from the wafer surface, and the number of LSTDs having a size of 50 nm or more may be 0.06 number/cm$^2$ or less.

Thus, the silicon wafer of the present invention can be a silicon wafer containing extremely fewer defects compared with even an epitaxial wafer, which has conventionally been considered a silicon wafer containing fewest defects, in spite of not forming an epitaxial layer. Therefore, it can be a wafer that is sufficiently adoptable for the latest extremely highly integrated devices or those expected to be produced in future.

In this case, $1.0 \times 10^8$ number/cm$^3$ or more of BMDs may exist in a bulk portion of the aforementioned silicon wafer.

If such a sufficient amount of BMDs exist in the bulk portion of the silicon wafer as described above, the wafer can be a wafer having sufficient gettering effect in addition to the surface layer portion containing few defects.

Alternatively, the bulk portion of the aforementioned silicon wafer can be made to have $1.0 \times 10^8$ number/cm$^3$ or more of BMDs by a heat treatment.

If such a sufficient amount of BMDs are precipitated in the bulk portion of the silicon wafer by a heat treatment as described above, impurities such as heavy metals in the wafer surface layer portion can be removed by a heat treatment. However, if the amount of BMD is too large, strength of the wafer may be degraded, and therefore the number is preferably $1 \times 10^{12}$ number/cm$^3$ or less.

In this ease, the aforementioned heat treatment can be a heat treatment in the device production step.

If a device production heat treatment is also used as a gettering heat treatment without separately performing a gettering heat treatment as described above, the operation can be simplified and the gettering effect can be more easily obtained.

The present invention also provides a method for determining production conditions of a silicon single crystal, which comprises pulling one or more nitrogen-doped silicon single crystals by the Czochralski method while varying a ratio V/G of pulling rate V and temperature gradient G at a solid-liquid interfaces and/or a passage time PT for a temperature zone where grown-in defects agglomerate, producing silicon wafers from the silicon single crystal or crystals, subjecting the silicon wafers to a predetermined heat treatment, measuring a characteristic value of the silicon wafers to determine acceptability of the wafers based on a predetermined characteristic value, obtaining correlation between the acceptability and V/G and PT, and determining production conditions based on the correlation.

If the production conditions of single crystals are determined by pulling one or more nitrogen-doped silicon single crystals by the Czochralski method while varying V/G and/or PT, producing silicon wafers, and determining the production conditions according to the correlation between the acceptability based on the characteristic value of the silicon wafers after the heat treatment and V/G and PT as described above, there can be surely produced silicon single crystals that provide nitrogen-doped annealed wafers showing a low defect density even under severe examination conditions and little fluctuation thereof depending on the production condition.

Furthermore, if samples are obtained with various V/G and PT by using a suitable HZ (hot zone: internal structure of furnace in a CZ pulling apparatus) in the manner described above, it becomes sufficient to subsequently produce HZ only once, and single crystals containing extremely few grown-in defects can be surely obtained without producing HZ many times as the conventional practice. Thus, there is also obtained an advantage of reduced development cost.

In this case, the characteristic value of silicon wafers may be a grown-in defect density or electrical characteristic of the silicon wafer surface.

If the grown-in defect density or electrical characteristic of the silicon wafer surface is measured as the characteristic value of the silicon wafer and used as the standard for judgment of acceptability, silicon single crystals having a desired grown-in defect density or electrical characteristic can be stably produced by producing silicon single crystals with the production conditions determined based on the standard.

In this case, the measurement of the characteristic value of the silicon wafer can be performed after the silicon wafer surface undergone the aforementioned heat treatment is polished for a predetermined amount.

If the measurement of the characteristic value of the silicon water is performed after the silicon wafer surface undergone the heat treatment is polished for a predetermined amount as described above, a characteristic value at a position of a predetermined depth from the wafer surface can be easily evaluated, even when, for example, the measurement of the characteristic value is performed by using an apparatus that can measure grown-in defects only for the wafer surface.

In this case, when a nitrogen-doped silicon single crystal is pulled by the Czochralski method, nitrogen concentration and oxygen concentration in the silicon single crystal are preferably determined beforehand.

This is because the nitrogen concentration and oxygen concentration are parameters that closely relate to the BMD density, generation amount of N—O donors etc., and hence in order to obtain desired values thereof, it is preferable to determine the nitrogen concentration and oxygen-concentration beforehand.

In this case, the nitrogen concentration and oxygen concentration can be determined based on the desired BMD density.

This is because the nitrogen-concentration and oxygen concentration are parameters that directly relate to the BMD density, and they are preferably adjusted to suitable levels, since unduly high oxygen concentration may cause problems such as large size of grown-in defects, while a higher oxygen concentration provides higher BMD density.

In this case, the aforementioned nitrogen concentration can be determined based on the desired generation amount of the N—O donors.

This is because the nitrogen concentration is a value closely relating to the generation amount of the N—O donors, and if too many N—O donors are generated, a silicon single crystal of a desired resistivity may not be obtained.

In this case, when a silicon single crystal doped with nitrogen is pulled by the Czochralski method, it is preferably pulled under such conditions that at least the center of the crystal should become a V-rich region.

This is because, if an I-rich region and a V-rich region are intermingled in a plane of the wafer produced from the pulled crystal, it becomes difficult to eliminate the defects existing in the I-rich region such as the dislocation clusters by a heat treatment.

In this case, when a silicon single crystal doped with nitrogen is pulled by the Czochralski method, it is preferably pulled under such conditions that dislocation clusters are not generated over the entire plane for the radius direction of the pulled crystal.

This is because, in order to eliminate the defects that are difficult to be eliminated by a heat treatment such as dislocation clusters, which exist in the I-rich region, it is preferred that the crystal should be pulled under such conditions that dislocation clusters are not generated over the entire plane for the radius direction of the pulled crystal by controlling the pulling conditions such as V/G.

Furthermore, in the method for determining pulling conditions according to the present invention, the aforementioned change of PT can be attained by changing the pulling rate V during the pulling of silicon single crystal.

By using such a method, portions produced with various values of PT can be obtained in one silicon single crystal, and at least one type of HZ to be used is sufficient. Therefore, it is not required to design and produce various kinds of HZ for the confirmation.

In this case, it is preferable to perform a heat treatment at a temperature of 1150° C. or higher for 1 hour or more as the aforementioned predetermined heat treatment.

This is because, if the silicon single crystal produced with the production conditions according to the present invention is subjected to a heat treatment at a temperature of at least 1150° C. for 1 hour or more, a silicon wafer containing extremely few defects at a level that has never existed so far can be obtained.

The present invention also provides a method for producing a silicon wafer, which comprises producing a silicon single crystal using production conditions determined by the aforementioned method for determining production conditions of a silicon single crystal according to the present invention, and producing a silicon wafer from the silicon single crystal.

If a silicon wafer is produced by using a silicon single crystal that has been produced under conditions determined according to the present invention as described above, a silicon wafer containing extremely few defects at a level that has never been obtained so far can be stably obtained without fluctuation of their quality.

In this case, the produced silicon water is preferably subjected to a heat treatment, and it is more preferable to perform a heat treatment at a temperature of 1150° C. or higher for 1 hour or more as the aforementioned heat treatment.

If the silicon wafer produced from a silicon single crystal that has been produced under conditions determined according to the present invention is subjected to a heat treatment, particularly preferably at a temperature of 1150° C. or higher for 1 hour or more as described above, the silicon water can be surely made into a silicon wafer having the predetermined characteristic value.

As for the conditions for the heat treatment, it is preferably performed at a temperature of 1300° C. or lower for 10 hours or less, if durability of heat treatment furnace, influence on wafer quality and cost are taken into consideration.

The present invention further provides a method for producing a silicon wafer comprising producing a silicon wafer from a silicon single crystal pulled by the Czochralski method with nitrogen doping and subjecting the silicon wafer to a heat treatment, wherein the silicon single crystal is pulled so that a ratio V/G of a pulling rate V of the single crystal and a temperature gradient G at solid-liquid interface, and a passage time PT for a temperature zone where grown-in defects agglomerate should be lower than a predetermined value of V/G and shorter than a predetermined time of PT, respectively, that are uniquely defined by predetermined nitrogen concentration and oxygen concentration in the silicon single crystal, conditions of heat treatment to which the silicon wafer is subjected, and grown-in defect density of the silicon wafer obtained after the heat treatment.

If the nitrogen concentration and oxygen concentration in the silicon single crystal, conditions of heat treatment to which the silicon wafer is subjected, and grown-in defect density of the silicon wafer obtained after the heat treatment are predetermined, and a silicon single crystal is pulled with V/G and PT respectively lower, and shorter than the values thereof uniquely defined by the above predetermined conditions as described above, a silicon wafer can be obtained with defects fewer than any conventional low defect wafers depending on its production conditions, and the silicon wafer show little quality fluctuation.

In this case, the aforementioned nitrogen concentration and oxygen concentration are preferably defined to be $1 \times 10^{13}$ to $2 \times 10^{14}$ number/cm$^3$ and 12–18 ppma (JEIDA: Japan Electronic Industry Development Association standard), respectively, and the aforementioned heat treatment conditions are preferably represented as a heat treatment at 1200° C. for 1 hour or more, or at 1150° C. for 2 hours or more.

If the nitrogen concentration and the oxygen concentration of the silicon single crystal are selected to be within the aforementioned ranges, the problems caused by increase of grown-in defect size, generation of N—O donors and so forth can be prevented, and if a silicon wafer produced in such a manner is subjected to a heat treatment at 1200° C. for 1 hour or more, or at 1150° C. for 2 hours or more, there can be produced a silicon wafer containing extremely few defects at a level never existed so far.

Since the wafer of the present invention contains extremely few defects, it can be used for the latest devices or devices to be produced in future, which are severely restricted as for defects, without causing degradation of device characteristics and yield reduction. Further, since the heat treatment conditions for reducing defects are similar to or less severe than those for the conventional annealed wafers, any costly process, such as argon annealing+ oxidation treatment, is not required. Further, by producing an SOI wafer utilizing the surface layer-portion of the present invention, which contains extremely few defects, as an SOI (Silicon On Insulator) layer, it also becomes possible to produce devices of higher performance and function. Furthermore, according to the method of the present invention, various samples of V/G and passage time are obtained in a suitable HZ, and thus it is sufficient to subsequently produce HZ only once, In addition, single crystals and silicon wafers containing extremely few grown-in defects can be surely obtained.

BEST MODE FOR CARRYING OUT THE INVENTION

Figure 1:
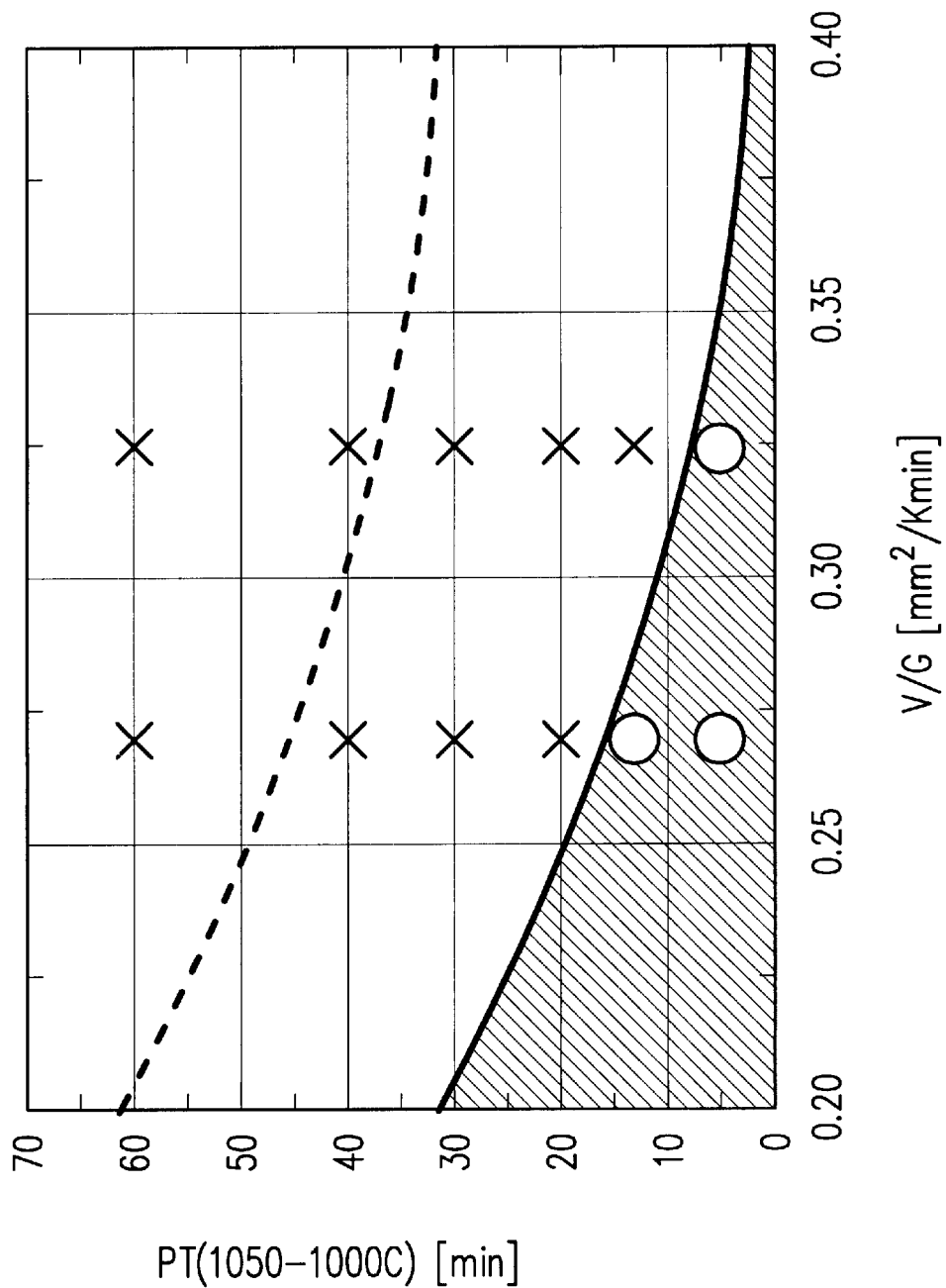
FIG. 1 is a correlation diagram showing relationship of V/G and PT during pulling of crystal and yield of good silicon wafers for silicon wafers subjected to annealing of 1150° C./2 h.

Hereafter, embodiments of the present invention will be explained in detail. However, the present invention is not limited to these.

The inventors of the present invention assiduously cumulated studies about the production conditions of a nitrogen-doped crystal that serves as a raw material of nitrogen-doped annealed wafers, with paying attention to, in particular, relationship between thermal history of the crystal and grown-in defects. As a result, they found for the first time that, although grown-in defects were strongly influenced by thermal history of crystal also in a nitrogen-doped crystal as in a non-nitrogen-doped crystal, the influencing temperature zones were different among them. And they further found that, based on the above finding there can be produced a nitrogen-doped annealed wafer that shows few grown-in defects even when it was examined under severe conditions and also shows little fluctuation due to the production condition by controlling grown-in defects of nitrogen-doped crystal used as a raw material of the nitrogen-doped annealed wafer. Thus, they accomplished the present invention.

Prior to the explanation of the present invention, technical terms, in particular, those used for major types of grown-in defects, will be explained beforehand.

(1) FPD (Flow Pattern Defect)

When a wafer sliced from a grown silicon single crystal ingot is subjected to etching with a mixture of hydrofluoric acid and nitric acid to remove a surface damaged layer, and then surface etching with a mixture of $K_2Cr_2O_7$, hydrofluoric acid and water (Secco etching), pits and a ripple pattern are formed on the wafer surface. This ripple pattern is called FPD, and a higher FPD density on the wafer surface caused more frequent oxide dielectric breakdown voltage failure (see Japanese Patent Application Laid-open (Kokai) No. 4-192345).

(2) LSTD (Laser Scattering-Tomography Defect)

For example, after a wafer is sliced from a grown silicon single crystal ingot, and subjected to etching with a mixture of hydrofluoric acid and nitric acid to remove a surface damaged layer, the wafer is cleaved. When the cleaved surface is irradiated with an infrared light, scattered lights caused by defects present in the wafer can be observed by detecting lights emitted from the wafer surface. The light-scattering substances detected in this observation have already been reported in academic societies and so forth, and considered to be oxygen precipitates (see, J. J. A. P., Vol. 32, p.3679, 1993). More recent study also reported that they are octahedral voids (holes).

(3) COP (Crystal Originated Particle)

COP means a defect which degrades oxide dielectric breakdown voltage at the center of wafer, and which is revealed as FPD after the Secco etching, but is revealed as pits after SC-1 cleaning (cleaning with a mixture of $NH_4OH:H_2O_2:H_2O=1:1:10$), which serves as a selective etching solution. Pits of this type have a diameter of 1 $\mu$m or less, and detected by the light scattering method.

For the aforementioned nitrogen-doped annealed wafer, grown-in defect size and density of CZ crystal that serves as a base are very important first of all, and the annealing conditions are also important. Among them, as for the grown-in defect size and density of CZ crystal that serves as a base, conventional nitrogen-doped annealed wafers relied only on the effect of nitrogen, and it was noticed that optimization of other conditions were still inadequate. That is, nitrogen doping was just used with the conventional standard conditions (or only pulling rate was increased). However, even these conditions well eliminated defects compared with non-doped annealed wafers.

As parameters affecting grown-in defects other than the nitrogen concentration, thermal history during the crystal pulling and oxygen concentration can be expected. In this case, there are two types of thermal history of crystal. First, there is mentioned V/G, which is a ratio of pulling rate V and temperature gradient G at a solid-liquid interface, and it is considered a parameter determining point defect density before agglomeration at least for usual non-nitrogen-doped crystals. And second, there is the passage time PT for a temperature zone where the point defects agglomerate into grown-in defects, and this is a parameter that determines the agglomeration. When nitrogen is doped, attention must be paid to the fact that the above temperature zone is different from that of ordinary non-nitrogen-doped crystals (refer to Japanese Patent Application No. 11-243961).

Then, first, in order to investigate influence of thermal history during pulling of nitrogen-doped crystal on the size and density distribution of grown-in defects, the inventors of the present invention prepared 12 types in total of crystal samples with a predetermined nitrogen concentration of $3.9 \times 10^{13}$ number/cm$^3$ (calculated value for a shoulder position of crystal) and oxygen concentration of 13–15 ppma (JEIDA: Japan Electronic Industry Development Association standard), and two kinds of V/G during crystal growth of 0.27 and 0.325 [mm$^2$/Kmin] and 6 kinds of passage time for the agglomeration temperature zone, 5, 13, 20, 30, 40 and 60 [min], which were selected for a temperature range of 1050° C. to 1000° C. since this temperature range corresponded to the agglomeration temperature zone of crystals doped with nitrogen at a nitrogen concentration of $10^{13}$ order, and investigated the relationship between grown-in defect and thermal history. As a result, it was found that a smaller V/G and shorter passage time for agglomeration temperature zone provided both of smaller size and smaller density of the defects. That is, from the above result, it can be said that the grown-in defects of nitrogen-doped samples were also strongly influenced by the thermal history like non-doped samples.

Then, the samples were subjected to annealing of 1200° C./1 h or 1150° C./2 h in a 100% argon atmosphere, and grown-in defects (LSTDs) were evaluated by MO-601 for a depth of 5 μm from the surface. As a result, it was found that, with samples obtained with a smaller V/G and a shorter passage time, waters having extremely few defects were obtained, in which the density was 6 number/6" wafer (0.03 number/cm$^2$) for wafers undergone a heat treatment at 1200° C., or 10 number/6" wafer (0.06 number/cm$^2$) for wafers undergone a heat treatment at 1150° C., which levels had never been obtained conventionally.

Therefore, based on the above results, the sample containing a slightly larger amount of defects, which was subjected to the annealing of 1150° C./2 h, was used as a standard, that is, the LSTD level of 10 number/6" wafer (0.06 number/cm$^2$) or less was used as a criterion for determining acceptability to prepare a correlation diagram showing relationship with respect to V/G and the passage time PT as shown in FIG. 1. In FIG. 1, the plots represented with ○ indicate those satisfying the criterion of 10 number/6" wafer or less, and the plots represented with X indicate those not satisfying the criterion of 10 number/6" wafer or less. That is, if a nitrogen-doped silicon single crystal is produced by using pulling conditions falling into the hatched region shown in FIG. 1, a silicon wafer produced from the single crystal becomes a wafer containing extremely few defects at a level that has never been existed so far at least after annealing at 1200° C. for 1 hour or more or 1150° C. for 2 hours or more.

Further, while the aforementioned determination for acceptability was performed for defects existing within a depth of 5 μm from the surface, a non-defect region usually required should have a depth of about 3 μm from a wafer surface. Therefore, if there is selected a criterion that C-mode good chip yield for TZDB (Time Zero Dielectric Breakdown) characteristic (dielectric breakdown electric field was 8 MV/cm or higher), which is an oxide dielectric breakdown voltage characteristic, should be 95% or more for a surface obtained by polishing for a depth of 3 μm from a surface after a heat treatment at 1200° C. for 1 hour as the acceptability determination criterion, the acceptability determination criterion was moderated and therefore the boundary shifts upward, i.e., it is represented by the broken line shown in FIG. 1.

Figure 3:
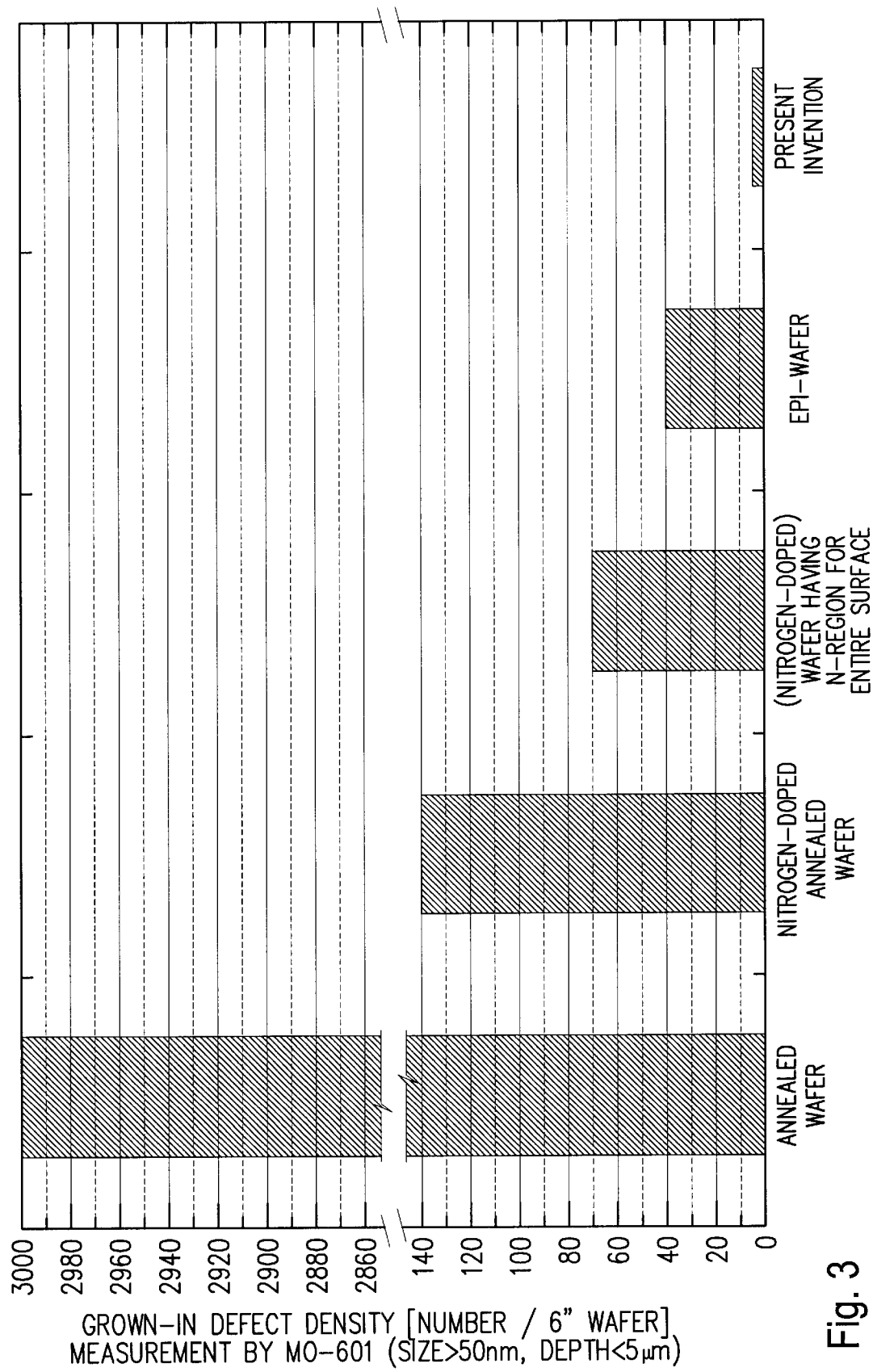
FIG. 3 is a comparison diagram showing comparison of grown-in defect densities of a silicon wafer of the present invention and conventional low defect silicon wafers.

Comparison of the grown-in defect densities of a wafer of the present invention containing extremely few defects and other conventional low defect crystals is shown in FIG. 3. As clearly seen from these results, it was found that the wafer of the present invention using the optimal nitrogen doped CZ wafer+argon annealing can be obtained as a wafer containing defects extremely fewer than those of any conventional low defect wafers depending on the production conditions therefor.

In order to optimize the production conditions of a nitrogen-doped CZ—Si single crystal with respect to the annealing conditions so as to produce a wafer containing extremely few defects, parameters that determine the size and density of grown-in defects were investigated first. The parameters that determine the size and density of grown-in defects include nitrogen concentration, oxygen concentration, and ratio V/G of pulling rate V and temperature gradient G at a solid-liquid interface, and passage time PT for a temperature zone where defects agglomerate as thermal history during pulling of crystal.

Among these, the oxygen concentration, first of all, is usually fixed in many cases according to users' specifications. Further, this is a parameter directly relating to the BMD density, and a higher oxygen concentration can provide a higher BMD density but increases the size of grown-in defects. Therefore, it is preferably fixed within a moderate range (for example, 12–18 [ppma], in particular, 13–15 [ppma]).

Further, a higher nitrogen concentration is more desirable, because the aforementioned agglomeration inhibition effect and oxygen precipitation promotion effect are increased. However, it may also enlarge the OSF ring region, on which secondary defects such as dislocation loops may further be generated, and may change resistivity due to generation of N—O donors by binding with oxygen. Thus, it cannot be made higher so much either. Therefore, it is also desirable to fix it within ascertain range (for example, about 1 to $20 \times 10^{13}$ [number/cm$^3$]), and not to use it for control of grown-in defects. The amount of generated N—O donors can be estimated from a difference in resistivity of a nitrogen-doped wafer measured before and after a heat treatment at about 500–800° C. for generating N—O donors.

Further, the nitrogen-concentration and oxygen concentration in a silicon single crystal are preferably adjusted to levels providing a desired BMD density within such ranges that the aforementioned problems should not be caused. For example, when BMDs of $1.0 \times 10^8$ [number/cm$^3$] or more is required, the oxygen concentration can be selected to be within the range of 12–18 ppma, and the nitrogen concentration can be selected to be within the range of $1 \times 10^{13}$ to $2 \times 10^{14}$ [number/cm$^3$].

Since the oxygen concentration and nitrogen concentration are determined beforehand as described above, the parameters that can be used for the control of grown-in defects as the practical crystal growth conditions should be V/G and the passage time PT for agglomeration temperature zone. In usual crystals, V/G is a parameter that influences the concentration of point defects before the agglomeration of grown-in defects.

Therefore, in order to determine these parameters, silicon wafers are first produced from each of silicon single crystals produced with different V/G or PT, or silicon single crystals produced with different V/G and PT. While these silicon single crystals pulled with different conditions may be pulled by changing the conditions of V/G and PT for every batch of pulling of silicon ingot, the change of PT condition may be obtained within a single ingot by changing the pulling rate during pulling of the ingot. In this method, V/G is determined by the initial pulling rate, and a portion corresponding to a certain PT, which is determined by a pulling rate of later stage, can be prepared as a certain portion of the crystal. Furthermore, in this method, it is sufficient to use at least one type of HZ, and it is not required to design and produce various types of HZ for the confirmation.

In this case, while G required for calculation of V/G and PT are usually calculated by using results of thermal analysis (simulation), it is preferable for such a case to use results of transient analysis taking specific heat of crystal into consideration. If PT is calculated based on steady-state analysis that does not take the specific heat into consideration, a gap may be generated for different diameters of crystals, Therefore, when results of steady-state analysis are used, it is preferable to perform an experiment for every diameter taking influence of specific heat into consideration and perform calibration based on its results.

Further, as G required for calculating V/G, it is preferable to use a value of G at a position as near the solid-liquid interface as possible for the calculation. In the present invention, an average for the range of from the melting point of silicon to 1400° C. is used. Further, the silicon angle crystal pulling operation was simulated by using FEMAG (global heat transfer analysis software, F. Dupret, P. Nicodeme, Y. Ryckmans, P. Wouters and M. J. Crochet, Int. J. Heat Mass Transfer, 33, 1849 (1990)) in its quasi steady-state-mode to calculate G.

Further, in order to control V/G and PT, it is necessary to obtain critical size and density of grown-in defects for obtaining the required characteristic value of wafers (for example, grown-in defect density, depth of defect-free layer, electrical characteristics of wafer surface (oxide dielectric breakdown voltage characteristics, etc.) by a desired heat treatment to which the produced wafer is subjected. Then, silicon wafers produced from silicon single-crystals obtained with various V/G and PT are subjected to annealing. The annealing conditions may be suitably selected as required. For example, it may be annealing at 1200° C. for 1 hour, which is performed for hydrogen annealed wafers etc., as a standard treatment, annealing at 1150° C. for 2 hours considering use of lower temperature in future and so forth. The annealing atmosphere can also be optionally selected from hydrogen, argon, mixed gas atmosphere thereof and so forth.

Then, a characteristic value of the wafers after the annealing is measured, their acceptability was determined by using a predetermined characteristic value as a standard, and correlation between the determined acceptability and V/G and PT. When the grown-in defect density is evaluated as the characteristic value of wafers, if an evaluation apparatus that enables evaluation of defects along the depth direction, for example, MO-601 (produced by Mitsui Mining and Smelting Co., Ltd.), is used, this apparatus enables evaluation of defects along the depth direction for a depth of about 5 µm. Therefore, if a defect-free layer of about 5 µm is desired, the evaluation can be performed by using this evaluation apparatus. Further, even when an apparatus that can evaluate only defects on the surface is used, the wafers after the annealing can be polished for a depth of desired defect-free layer and then measurement can be performed. Further, as the characteristic value of wafers, a good chip yield for oxide dielectric breakdown voltage such as TZDB and TDDB (Time Dependent Dielectric Breakdown) can also be used as a parameter. In any case, the acceptability determination of the characteristic value of wafers can be performed on the basis of an arbitrary value, and correlation between the acceptability determination and V/G and PT can be obtained based on the value.

FIG. 1 shows correlation of V/G and PT and grown-in defect density, where a grown-in defect density (LSTD density) of 10 number/6" wafer or less was used as a criterion for the acceptability determination. If a nitrogen-doped silicon single crystal is pulled with the conditions of V/G and PT selected from the hatched region shown in the correlation diagram, and a silicon wafer is produced from that single crystal and subjected to a predetermined heat treatment, a wafer having desired extremely few defects represented by a LSTD density of 10 number/6" or less will be obtained.

When a nitrogen-doped silicon single crystal is pulled with V/G-selected from the hatched region, it is preferably pulled so that at least the center portion of the crystal should become a V-rich region. This is because it becomes difficult to eliminate defects such as dislocation clusters existing in an I-rich region by a heat treatment, when an I-rich region is intermingled in a plane of the wafer produced from the pulled crystal.

As described above, if a range of production conditions enabling production of desired crystals is preliminarily determined based on the aforementioned correlation, there remains thereafter only design of HZ and growth conditions as required, and once of production of HZ and so forth is sufficient. Therefore, development cost would be reduced. As for the design of HZ, the pulling rate is first determined to be an arbitrary level, and then HZ can be analyzed and designed so that V/G and the passage time for agglomeration temperature zone should be within the predetermined ranges. For example, if the pulling rate is determined to he 1.0 [mm/min] and G is determined to be 3.5 [K/mm], V/G is calculated to be 0.286 [mm$^2$/Kmin]. Therefore, if the region of 1050–1000° C. is designed to be a length of 3 cm or less so that the passage time for the agglomeration temperature zone should be at least 30 minutes or less (about 35 minutes is considered to be allowable in an actual operation), the above intended design should be satisfied.

When such an HZ (referred to as HZ-A) was actually produced, a crystal was grown with a pulling rate, oxygen concentration and nitrogen concentration adjusted to be 1.0 [mm/min], about 14 [ppma] and 5×10$^{13}$ [number/cm$^3$], respectively, and a silicon wafer was produced and subjected to argon annealing at 1200° C. for 1 hour, a crystal free from COPs having a size of 0.09 µm or more at a position of a depth of 3 µm from the wafer surface could be obtained.

By the way, there may be a case where it is desired to change the oxygen concentration and nitrogen concentration. In such a case, if the change corresponds to use of a lower oxygen concentration (for example, a case where few BMDs are allowable) or a higher nitrogen concentration (for example, a case where N—O donors cause no problem), it does not need so much care. This is because, in such a case, the boundary line in the correlation diagram for V/G and the passage time obtained above for determining if defects can be eliminated or not shifts to an advantageous direction (upward direction in FIG. 1), and thus production can be performed with the already produced and established HZ and operation conditions. However, if the change corresponds to use of a higher oxygen concentration (for example, a case where more BMDs are desired) or a lower nitrogen concentration (for example, a case where defects unique to nitrogen may constitute a disturbance), care must be paid, and the boundary line shift toward the disadvantageous direction. Therefore, in such a case, it is desirable to newly obtain a boundary line for a silicon single crystal in the disadvantageous side of the boundary line through a similar experiment by producing a crystal with changing V/G and PT. In this case, since there are already basic data, the kinds of samples may be fewer.

Hereafter, the present invention will be specifically explained with reference to the following examples and comparative examples. However, the present invention is not limited to these.

EXAMPLE 1

First, silicon single crystals of a diameter of 6 inches, p-type, resistivity of 10 Ω·cm and crystal orientation of <100> were pulled with changing V/G and the agglomeration temperature zone passage time PT, and processed into mirror-polished wafers in a conventional manner. V/G was adjusted to be 0.27 and 0.325 [mm$^2$/Kmin] (G for V/G was calculated by performing simulation in the quasi steady-state mode of the aforementioned FEMAG), and the passage time for the agglomeration temperature zone (1050–1000° C.) was adjusted at six kinds of levels, 5, 13, 20, 30, 40 and 60 [min]. These silicon single crystals were produced with changing PT by a method of changing the pulling rate V during the pulling, and the nitrogen concentration was controlled to be 3.9×10$^{15}$ [number/cm$^3$](calculated value at a shoulder position of crystals) and the oxygen concentration was controlled to be 13–15 ppma (JEIDA).

Specifically, the crystals were first pulled at a pulling rate V1 (1.0 or 1.2 mm/min) for a length of 50 cm of the body from the crystal shoulder, then the pulling rate was rapidly changed from V1 to V2 (pulling rate selected from the range of 1.8–0.3 mm/min) during the pulling for the length of 50 cm to 51 cm, so that the diameter should not be changed as much as possible, and then the crystals were pulled at V2 for a length of 51 cm or more.

Since G during the pulling of crystal is considered to be substantially constant except for a portion of the length of about 10 cm from the crystal head, V/G is determined by V1 and PT is determined by V2 for a position within a length of 37–50 cm of the crystal body during the pulling. Therefore, if a plurality of crystals are pulled with conditions in which V2 is varied, there can be obtained crystals for which V/G is constant but PT is different. The position at a length of 37 cm of the body referred to herein means a position at which the temperature of the crystal is 1050° C. (upper limit of the agglomeration temperature zone) when the crystal is pulled for 50 cm. Further, since an OSF ring is generated for the length of about 48 cm to 50 cm due to the rapid change of the pulling rate, a portion of the lengths of about 37–45 cm must be used in order to eliminate the influence of the OSF ring.

Thus, a plurality of crystals were pulled with conditions in which V2 was varied according to the method in which the pulling rate was rapidly changed, and wafers were sliced from the crystals at a position within the length of 37–45 cm of the body to produce mirror-polished wafers obtained with identical V/G (at two kinds of levels in this example) and different PT.

Figure 4:
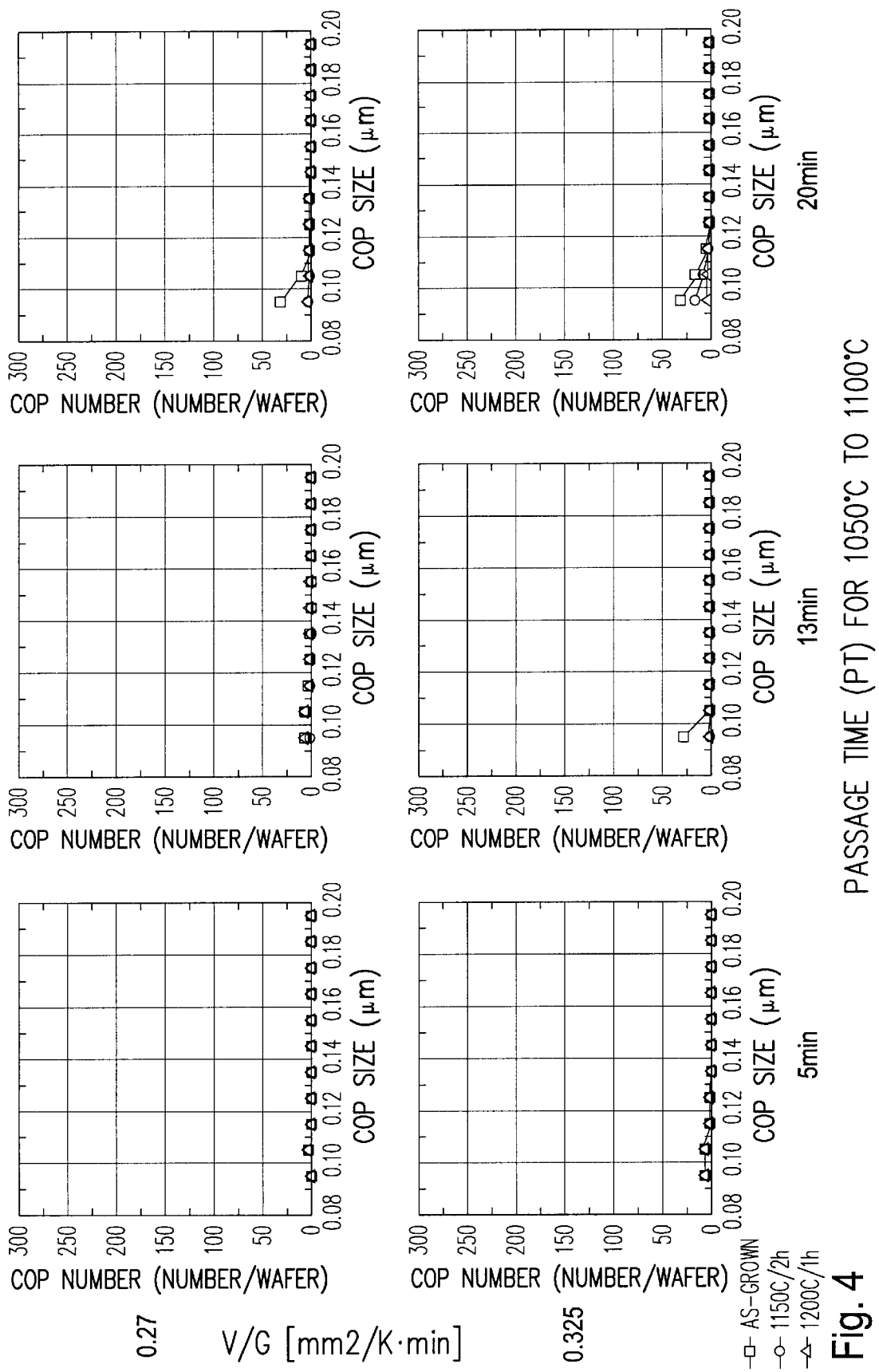
FIG. 4 shows relationship of V/G, PT and annealing heat treatment conditions and COP before SC-1 cleaning.
Figure 5:
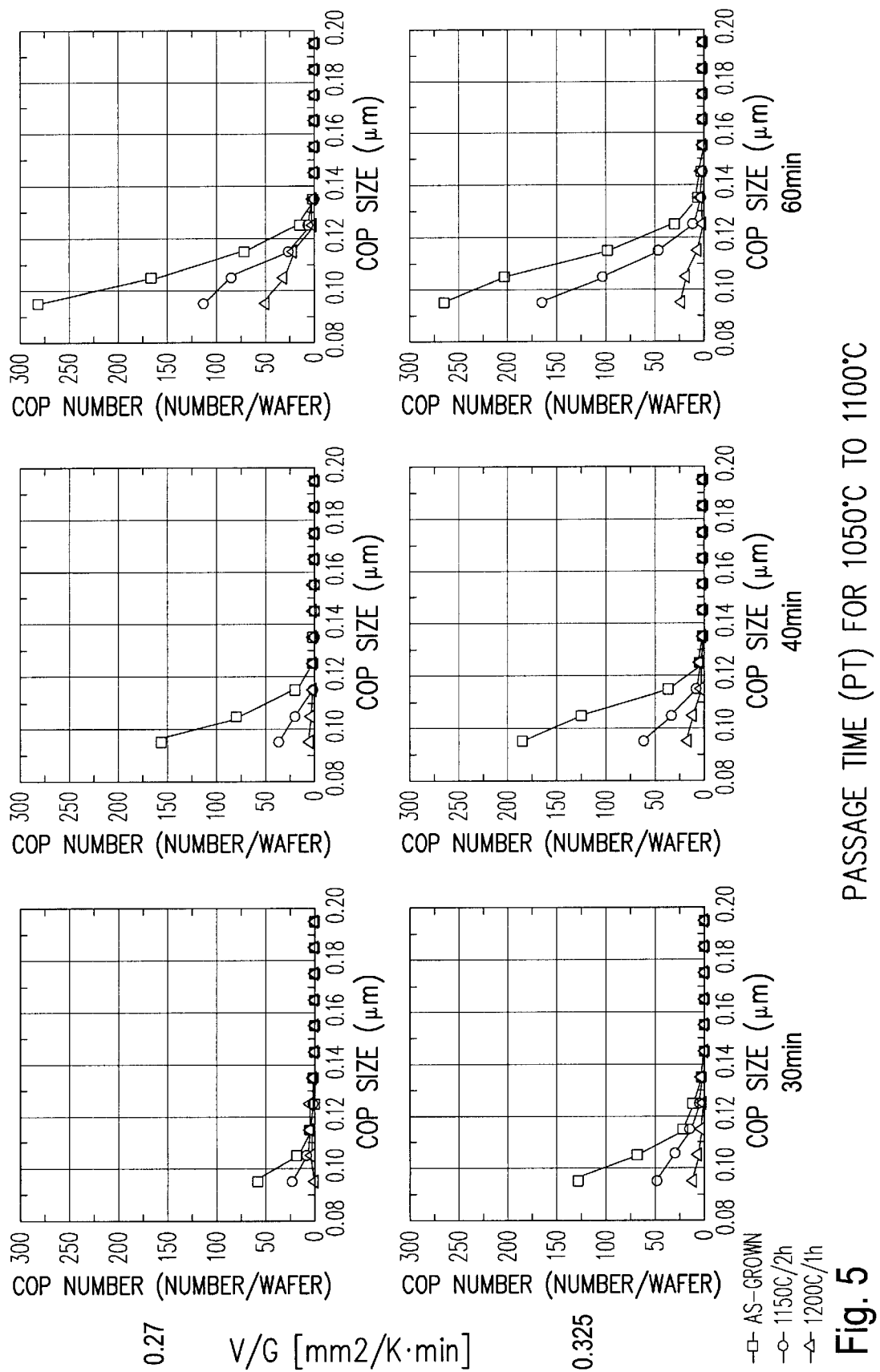
FIG. 5 shows relationship of V/G, PT and annealing heat treatment conditions and COP before SC-1 cleaning.

COPs of the obtained wafers in the as-grown state were measured (measurement apparatus:. SP-1 produced by KLA Tencor Co., measurable COP size: 0.09 μm or more). As a result, COPs showed clear correlation with respect to the thermal history, and a higher V/G value and a longer agglomeration temperature zone passage time PT provided a larger size and a larger density (FIG. 4, FIG. 5).

These wafers were subjected to argon annealing under either one of two kinds of conditions (1200° C./1 hour and 1150° C./2 hours). The required COP-free region was determined to have a depth of 3 μm from the surface, and the surfaces were polished by 3 μm. Then, COPs of a size of 0.09 μm or more existing on the polished surfaces (namely, at a depth of 3 μm from the original wafer surface) were measured. The results are also shown in FIGS. 4 and 5.

Then, in order to actualize COPs having a size of less than 0.09 μm that could not be detectable by the measurement apparatus, measurement was performed again after repetition of cleaning with SC-1 cleaning solution. Further, COPs of wafers before the heat treatment and after repetition of cleaning with SC-1 cleaning solution were also measured by using other wafers. The results are shown in FIGS. 6 and 7.

Figure 6:
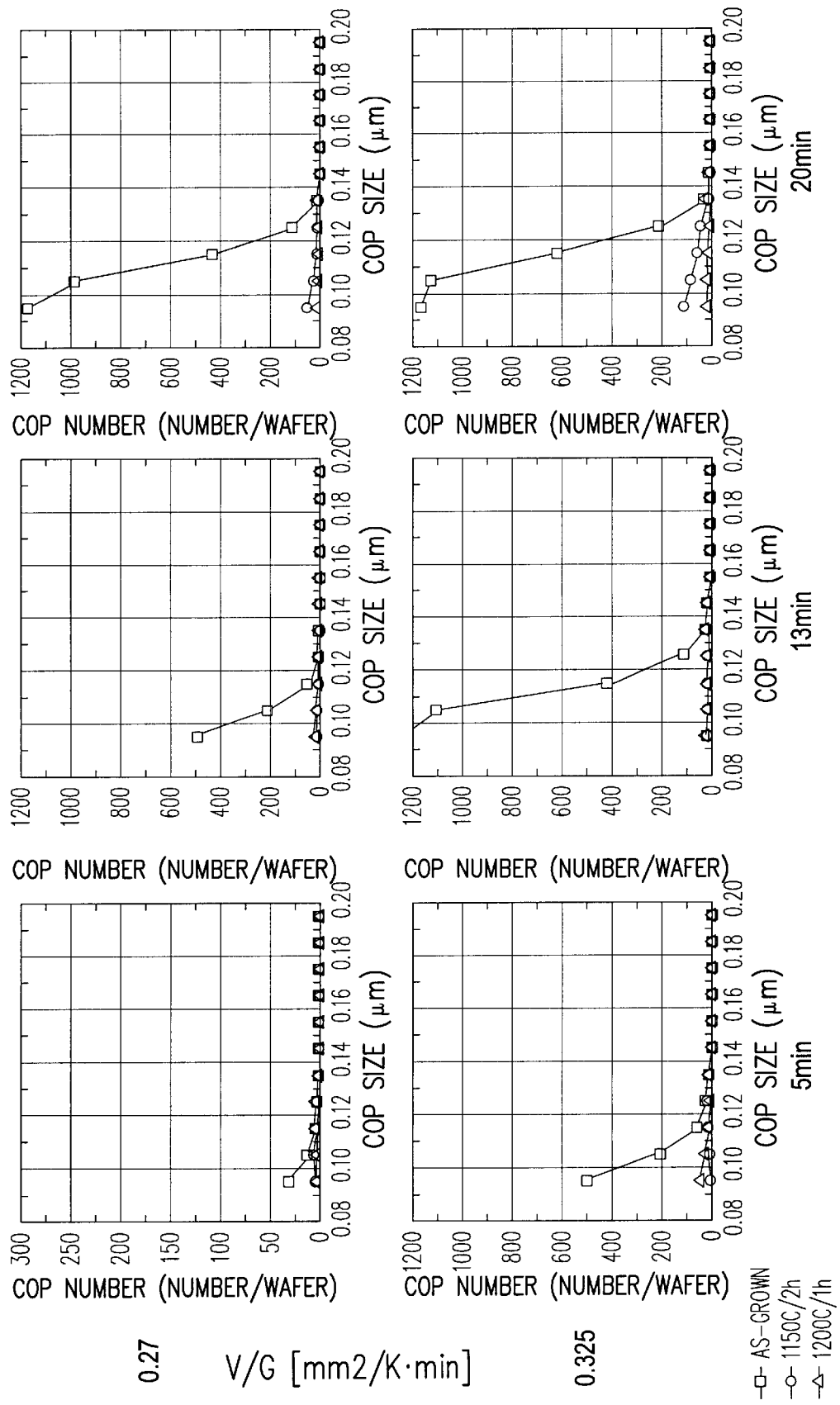
FIG. 6 shows relationship of V/G, PT and annealing heat treatment conditions and COP after SC-1 cleaning.
Figure 7:
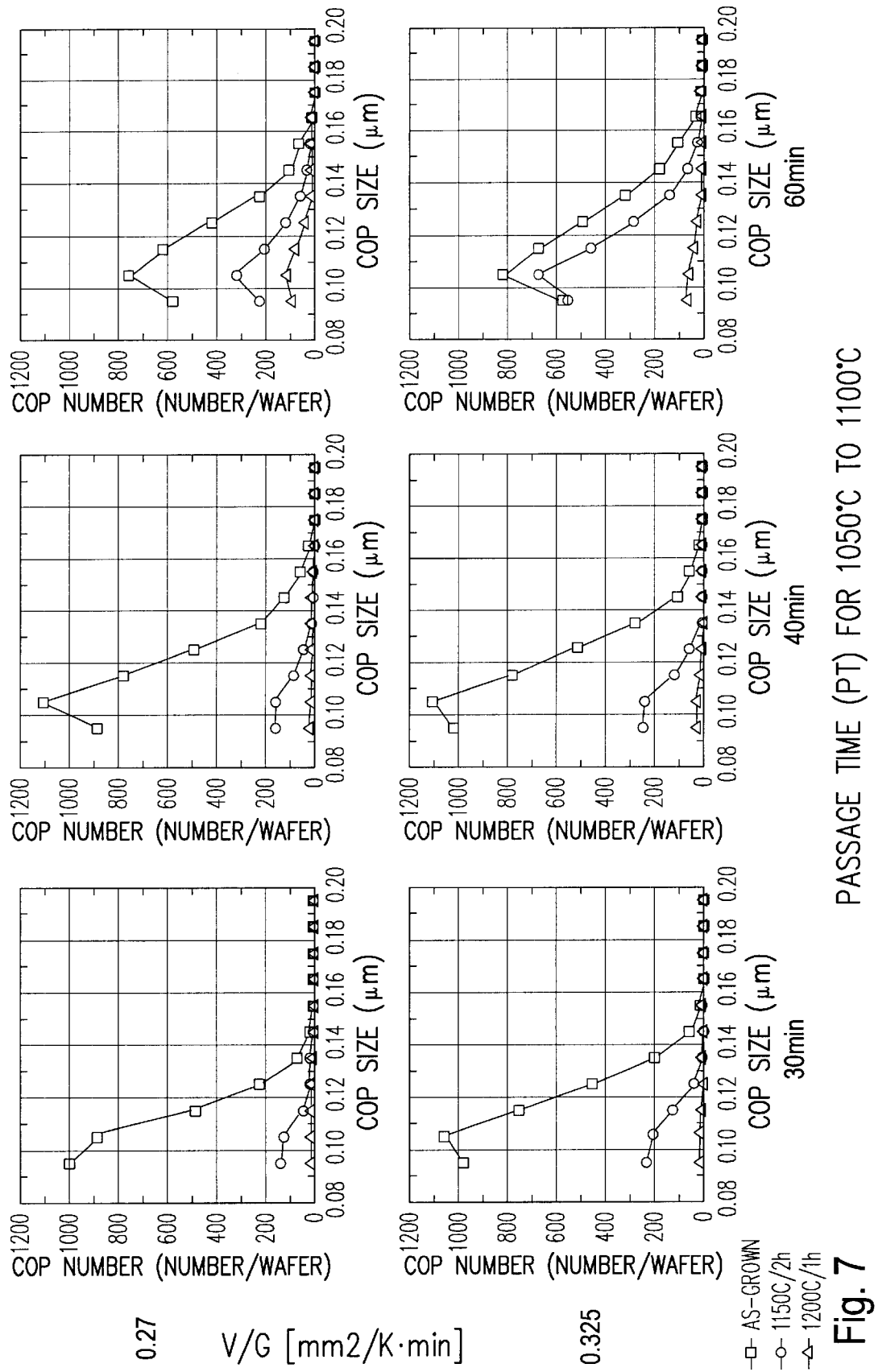
FIG. 7 shows relationship of V/G, PT and annealing heat treatment conditions and COP after SC-1 cleaning.

As seen from the results shown in FIGS. 6 and 7, COPs were well eliminated in samples undergone the annealing of 1200° C./1 h and obtained with V/G of 0.27 [mm$^2$/Kmin] and a passage time PT of 40 minutes or less, or V/G of 0.325 [mm$^2$/Kmin] and a passage time PT of 30 minutes or less, while COPs were considerably eliminated in samples undergone the annealing of 1150° C./2 h obtained with V/G of 0.27 [mm$^2$/Kmin] and a passage time PT of 20 minutes or less, or V/G of 0.325 [mm$^2$/Kmin] and a passage time PT of 13 minutes or less.

Then, a COP level of 70 number/wafer after the remeasurement was used as a criterion for the acceptability determination to prepare graphs representing the correlation with respect to V/G and PT. The graph for silicon wafers undergone the heat treatment of 1150° C./2 h was shown in FIG. 1 (solid line), and the graph for silicon wafers undergone the heat treatment of 1200° C./1 h was shown in FIG. 2, respectively. From these graphs, it can be seen that, if a silicon single crystal is pulled under a condition indicated by a position below each of the boundary lines of FIGS. 1 and 2 and a wafer is produced from the crystal and subjected to each of the heat treatments, a wafer in which a region for a depth of 3 μm is substantially free from voids can be obtained.

EXAMPLE 2

An oxide film was formed on a surface of a silicon wafer produced under the same conditions as in Example 1 (wafer undergone the heat treatment and polishing for a depth of 3 μm), and oxide dielectric breakdown voltages (TZDB, TDDB) of the wafer were measured under the following conditions. Then, graphs representing correlation with V/G and PT were prepared with a criterion for the acceptability determination that 95% of C-mode good chip yield for TZDB (dielectric breakdown electric field: 8 MV/cm or more, and 95% of □-mode good chip yield (charge amount at the time of dielectric breakdown was 25 C/cm$^2$ or more) were both satisfied.

The measurement conditions for TZDB and TDDB are shown below.

TZDB Measurement Conditions

Oxide film thickness (25.5 [nm]), gate area (8 [mm$^2$]), current in decision (1 [mA]), measurement number (100 [dot/wafer]).

TDDB Measurement Conditions

Oxide film-thickness (25.5 [nm]), gate area (4 [mm$^2$]), stress current density (0.01 [A/cm$^2$]), measurement number (100 [dot/wafer]), measurement temperature (100° C.).

Figure 2:
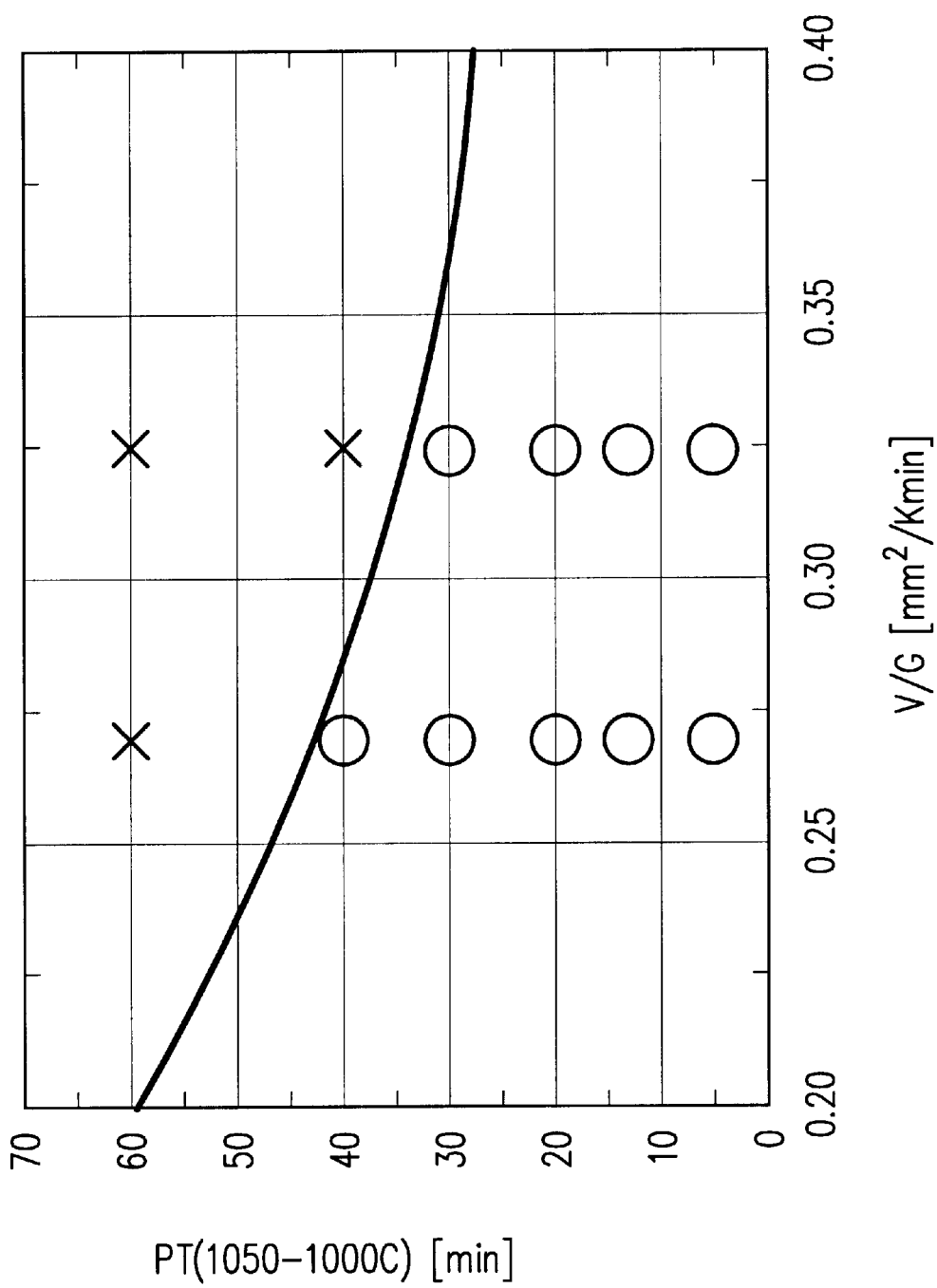
FIG. 2 is a correlation diagram showing relationship of V/G and PT during pulling of crystal and yield of good silicon wafers for silicon wafers subjected to annealing of 1200° C./1 h.

As a result, the correlation of oxide dielectric breakdown voltage characteristic with V/G and PT showed the almost same results as those of FIG. 1 and FIG. 2. This indicates that breakdown voltage can be predicted based on the result of COP measurement. Further, a tendency was also observed, in which wafers having a smaller COP size (obtained with a smaller V/G and shorter PT) showed a higher good chip yield for breakdown voltage after the annealing.

Based on these results, it can be said that, when a wafer showing a good chip yield of 95% or more for dielectric breakdown voltage at a depth of 3 μm is desired with the annealing conditions of 1200° C. and 1 hour, for example, a nitrogen-doped crystal can be produced with conditions represented by a position below the boundary line shown in FIG. 2. If the production conditions are determined as described above, nitrogen-doped annealed wafers with stable quality can be obtained.

EXAMPLE 3

Silicon single crystals of p-type, resistivity of 10 Ω·cm and crystal, orientation of <100> were pulled with conditions of V/G of 0.27 [mm$^2$/Kmin] (G for V/G was calculated by performing simulation in the quasi steady-state mode of the aforementioned FEMAG), and a passage time PT for the agglomeration temperature zone (1050–1000° C.) of 13 [min] as conditions indicated by a position below the boundary line (solid line) in FIG. 1, and processed into mirror-polished wafers. The nitrogen concentration was controlled to be 3.9×10$^{13}$ [number/cm$^3$] (calculated value at a shoulder position of crystals) and the oxygen concentration was controlled to be 13–15 ppma (JEIDA) Then, these wafers were subjected to annealing in a 100% argon atmosphere under either one of two kinds of conditions 1200° C./1 hour and 1150° C./2 hours, and grown-in defects (LSTDs) having a size of 50 nm or more existing in a portion of a depth of 5 μm from the surface were measured by using MO-601. As a result, it was found that wafers having extremely few defects, i.e., 6 number/6" wafer (about 0.03 number/cm$^2$), were obtained after the heat treatment at 1200° C., and those heaving the defects at a level of 10 number/6" wafer (about 0.06 number/cm$^2$) were obtained after the heat treatment at 1150° C.

Comparative Example

As a comparative experiment of Example 3, grown-in defects (LSTDs) having a size of 50 nm or more and existing in a portion of a depth of 5 μm from the surface were measured for 4 types of conventional low defect wafers (6 inches, p-type, resistivity: 10–20 Ω·cm). The results of the measurement are shown in FIG. 3 together with the results of Example 3. The production conditions of these four types of low deject wafers are as follows.

Annealed Wafer

A wafer obtained from a usual CZ wafer produced with a pulling rate of about 1 mm/min by subjecting it to hydrogen annealing at 1200° C. for 1 hour.

Nitrogen-doped Annealed Wafer

A wafer obtained from a nitrogen-doped wafer produced with V/G 0.51 [mm$^2$/Kmin] (G for V/G was calculated by performing simulation in the quasi steady-state rode of the aforementioned FEMAG), and PT of 14 [min] (nitrogen concentration: 4×10$^{13}$ [number/cm$^3$], oxygen concentration: 15 ppma) by subjecting it to hydrogen annealing at 1200° C. for 1 hour.

Nitrogen-doped Wafer Having N-region for Entire Plane

A CZ wafer having a nitrogen concentration of 4×10$^{13}$ [number/cm$^3$] and pulled under such conditions that the entire plane should become an N-region.

Epitaxial Wafer

An epitaxial wafer obtained by forming an epitaxial layer having a thickness of 7 μm at 1125° C. using trichlorosilane as the raw material gas on a usual CZ wafer produced with a pulling rate of about 1 mm/min.

From the results shown in FIG. 3, it can be seen that all of the conventional low defect silicon wafers had more defects on the wafer surfaces compared with the silicon wafer of the present invention. Further, as described above, the conventional nitrogen-doped wafers suffer from a drawback of significant fluctuation in defect density for every production lot, and the epi-wafers suffer from a drawback that they require a step of forming an epitaxial layer.

The present invention is not limited to the embodiments described above. The above-described embodiments are mere examples, and those having the substantially same structure as that described in the appended claims and providing the similar functions and advantages are included in the scope of the present invention.

For example, the aforementioned embodiments were explained for cases where silicon single crystals having a diameter of 6 inches were grown. However, the present invention is not limited to them, and can also be applied to silicon single crystals having a diameter of 8–16 inches or larger.

Further, the present invention can of course be used for the so-called MCZ method in which a horizontal magnetic field, vertical magnetic field, cusp magnetic field or the like is applied to silicon melt.

What is claimed is:

1. A silicon wafer, wherein an epitaxial layer is not formed on a surface, and LSTDs having a size of 50 nm or more existing in a surface layer portion are fewer than those existing in a surface layer portion of an epitaxial layer of a silicon epitaxial wafer.

2. The silicon wafer according to claim 1, wherein the surface layer portion is a region having a depth of at least 5 μm from the wafer surface.

3. The silicon wafer according to claim 1, wherein a bulk portion of the silicon wafer has 1.0×10$^8$ number/cm$^3$ or more of BMDs.

4. The silicon wafer according to claim 1, wherein a bulk portion of the silicon wafer is made to have 1.0×10$^8$ number/cm$^3$ or more of BMDs by a heat treatment.

5. The silicon water according to claim 4, wherein the heat treatment is a heat treatment in a device production step.

6. A silicon wafer, wherein an epitaxial layer is not formed on a surface, and number of LSTDs having a size of 50 nm or more existing in a surface layer portion is 0.23 number/cm$^2$ or less.

7. The silicon wafer according to claim 6, wherein the surface layer portion is a region having a depth of at least 5 μm from the wafer surface, and the number of LSTDs having a size of 50 nm or more is 0.06 number/cm$^2$ or less.

8. The silicon wafer according to claim 6, wherein a bulk portion of the silicon wafer has $1.0 \times 10^8$ number/cm$^3$ or more of BMDs.

9. The silicon wafer according to claim 6, wherein a bulk portion of the silicon wafer is made to have $1.0 \times 10^8$ number/cm$^3$ or more of BMDs by a heat treatment.

10. The silicon wafer according to claim 9, wherein the heat treatment is a heat treatment in a device production step.

11. A method for determining production conditions of a silicon single crystal, which comprises pulling one or more nitrogen-doped silicon single crystals by the Czochralski method while varying at least one of a ratio V/G of pulling rate V and temperature gradient G at a solid-liquid interface and a passage time PT for a temperature zone where grown-in defects agglomerate, producing silicon wafers from the silicon single crystal or crystals, subjecting the silicon wafers to a heat treatment, measuring a characteristic value of the silicon wafers to determine acceptability of the wafers based on a characteristic value, obtaining correlation between the acceptability and V/G and PT, and determining productions conditions based on the correlation.

12. The method for determining production conditions of a silicon single crystal according to claim 1, wherein the characteristic value of silicon wafers is a grown-in defect density or electrical characteristic of the silicon wafer surface.

13. The method for determining production conditions of a silicon single crystal according to claim 11, wherein the measurement of the characteristic value of the silicon wafer is performed after the silicon wafer surface undergone the heat treatment is polished.

14. The method for determining production conditions of a silicon single crystal according to claim 1, wherein, when a nitrogen-doped silicon single crystal is pulled by the Czochralski method, nitrogen concentration and oxygen concentration in the silicon single crystal are determined beforehand.

15. The method for determining production conditions of a silicon single crystal according to claim 14, wherein the nitrogen concentration and oxygen concentration are determined based on the desired BMD density.

16. The method for determining production conditions of a silicon single crystal according to claim 14, wherein the nitrogen concentration is determined based on a desired generation amount of the N—O donors.

17. The method for determining production conditions of a silicon single crystal according to claim 1, wherein, when a silicon single crystal doped with nitrogen is pulled by the Czochralski method, it is pulled under such conditions that at least the center of the crystal should become a V-rich region.

18. The method for determining production conditions of a silicon single crystal according to claim 1, wherein, when a silicon single crystal doped with nitrogen is pulled by the Czochralski method, it is pulled under such conditions that dislocation clusters are not generated over the entire plane for the radius direction of the pulled crystal.

19. The method for determining production conditions of a silicon single crystal according to claim 1, wherein the chance of PT is attained by changing the pulling rate V during the pulling of silicon single crystal.

20. The method for determining production conditions of a silicon single crystal according to claim 11, wherein a heat treatment at a temperature of 1150° C. or higher for 1 hour or more is performed as the heat treatment.

21. A method for producing a silicon wafer, which comprises producing a silicon single crystal using production conditions determined by a method for determining production conditions of a silicon single crystal according to claim 1, and producing a silicon wafer from the silicon single crystal.

22. The method for producing a silicon wafer according to claim 21, wherein the silicon wafer is subjected to a heat treatment.

23. The method for producing a silicon wafer according to claim 22, a heat treatment at a temperature of 1150° C. or higher for 1 hour or more is performed as the heat treatment.

24. A method for producing a silicon wafer comprising producing a silicon wafer from a silicon single crystal pulled by the Czochralski method with nitrogen doping and subjecting the silicon wafer to a heat treatment, wherein the silicon single crystal is pulled so that a ratio V/G of a pulling rate V of the single crystal and a temperature gradient G at solid-liquid interface, and a passage time PT for a temperature zone where grown-in defects agglomerate should be lower than a value of V/G and shorter than a time of PT, respectively, that are uniquely defined by nitrogen concentration and oxygen concentration in the silicon single crystal conditions of heat treatment to which the silicon wafer is subjected, and grown-in defect density of the silicon wafer obtained after the heat treatment.

25. The method for producing a silicon water according to claim 24, wherein the nitrogen concentration and oxygen concentration are defined to be $1 \times 10^{13}$ to $2 \times 10^{14}$ number/cm$^3$ and 12–18 ppma, respectively, and the heat treatment conditions are represented as a heat treatment at 1200° C. for 1 hour or more, or at 1150° C. for 2 hours or more.

\* \* \* \* \*

UNITED STATES PATENT AND TRADEMARK OFFICE
CERTIFICATE OF CORRECTION

PATENT NO.    : 6,599,360 B2
DATED         : July 29, 2003
INVENTOR(S)   : Makoto Iida et al.

It is certified that error appears in the above-identified patent and that said Letters Patent is hereby corrected as shown below:

<u>Title page,</u>
Between Items [65] and [51], insert the following item:
-- [30]  Foreign Application Priority Data
Jan. 25, 2000    (JP) ……………………….. 2000-15537 --.

Signed and Sealed this

Twenty-third Day of December, 2003

JAMES E. ROGAN
*Director of the United States Patent and Trademark Office*